United States Patent [19]

Dombrowski et al.

[11] Patent Number: 5,312,371

[45] Date of Patent: May 17, 1994

[54] METHOD OF MAKING A NEEDLE SLEEVE ASSEMBLY

[76] Inventors: Mitchell P. Dombrowski, 102 Merriweather, Grosse Point Farms, Mich. 48236; Robert A. Welch, 9573 Winterset Cir., Plymouth, Mich. 48170

[21] Appl. No.: 97,562

[22] Filed: Jul. 27, 1993

[51] Int. Cl.⁵ .............................................. A61M 5/32
[52] U.S. Cl. ..................................... 604/198; 604/263
[58] Field of Search ............... 604/198, 263, 192, 162, 604/187; 53/409

[56] References Cited

U.S. PATENT DOCUMENTS

| | | |
|---|---|---|
| 3,134,380 | 5/1964 | Armao . |
| 4,725,267 | 2/1988 | Vaillancourt .................. 604/198 |
| 4,795,432 | 1/1989 | Karczmer ...................... 604/263 |
| 4,846,809 | 7/1989 | Sims ............................... 604/263 |
| 4,978,344 | 12/1990 | Dombrowski et al. . |
| 4,994,041 | 2/1991 | Dombrowski et al. . |
| 5,114,409 | 5/1992 | Kole et al. ..................... 604/198 |

*Primary Examiner*—John D. Yasko
*Assistant Examiner*—Anthony Gutowski
*Attorney, Agent, or Firm*—Reising, Ethington, Barnard, Perry & Milton

[57] ABSTRACT

A method of making a self-capping needle and catheter assembly (10) includes placing a needle hub (16) and cap (34) on a pin with the pin extending through the passageways (24, 35) thereof. Two sheets of polymeric material (62) are placed about the hub (16) and the cap (34) with their edges welded together producing a sleeve (64) connected between the hub (16) and the cap (34). The sleeve (64) is then permanently stretched to a predetermined length. The cap (34), hub (16) and sleeve (64) are then placed on a needle (28) and the cap (34) is moved against the hub (16) folding the sleeve (64) therebetween for reception of the catheter assembly (14).

11 Claims, 3 Drawing Sheets

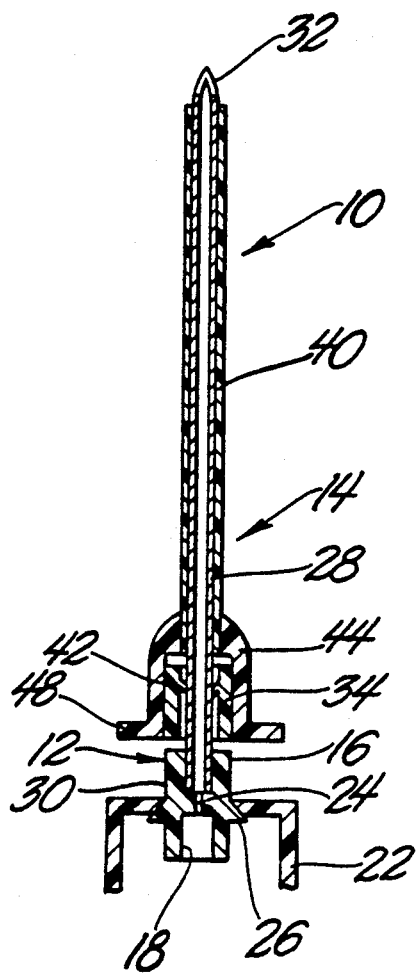
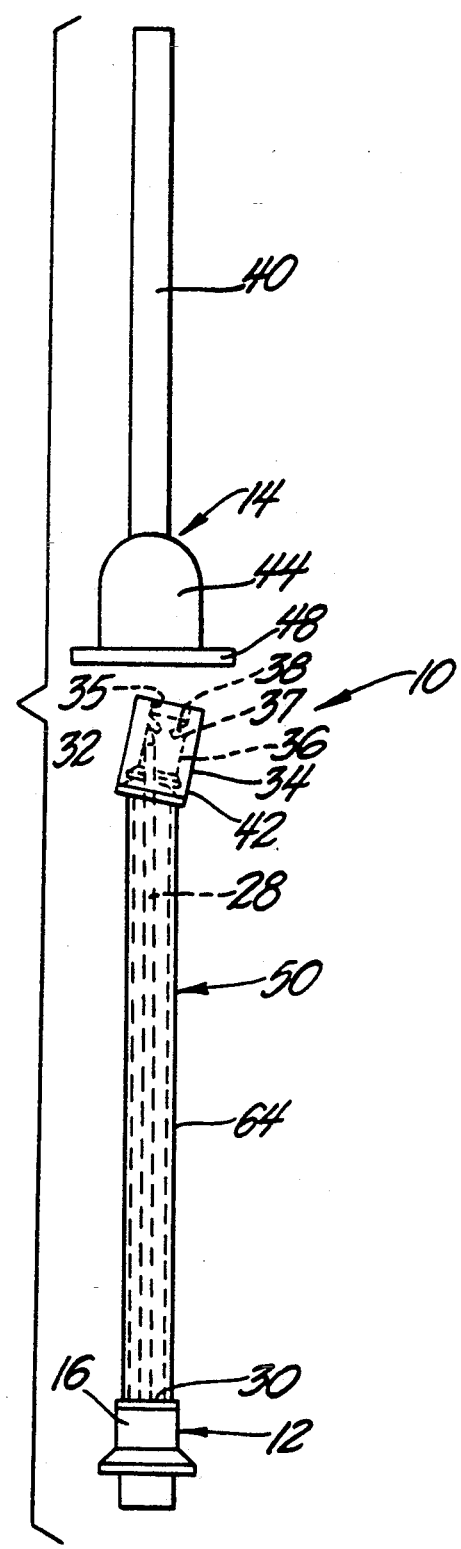

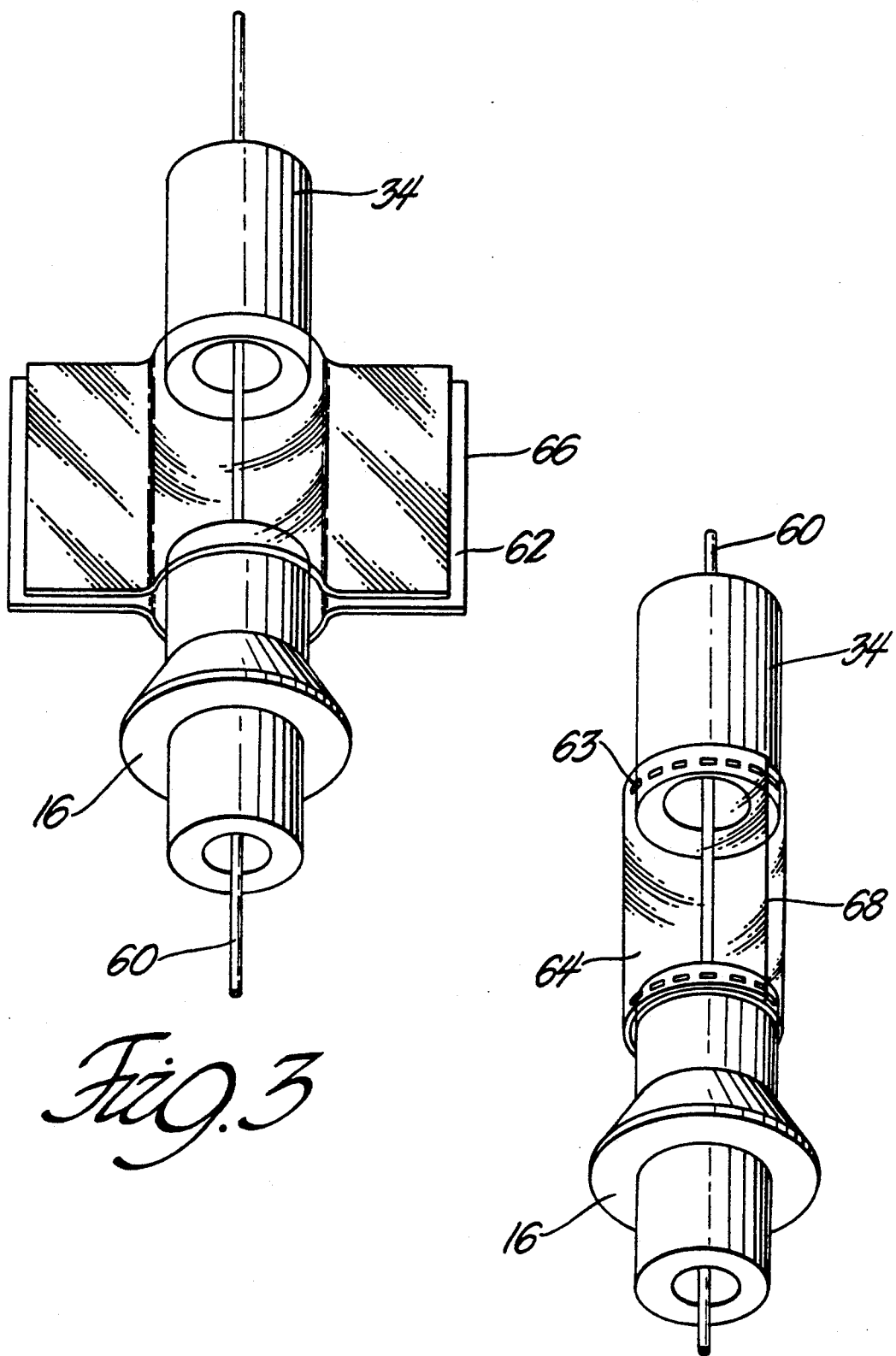

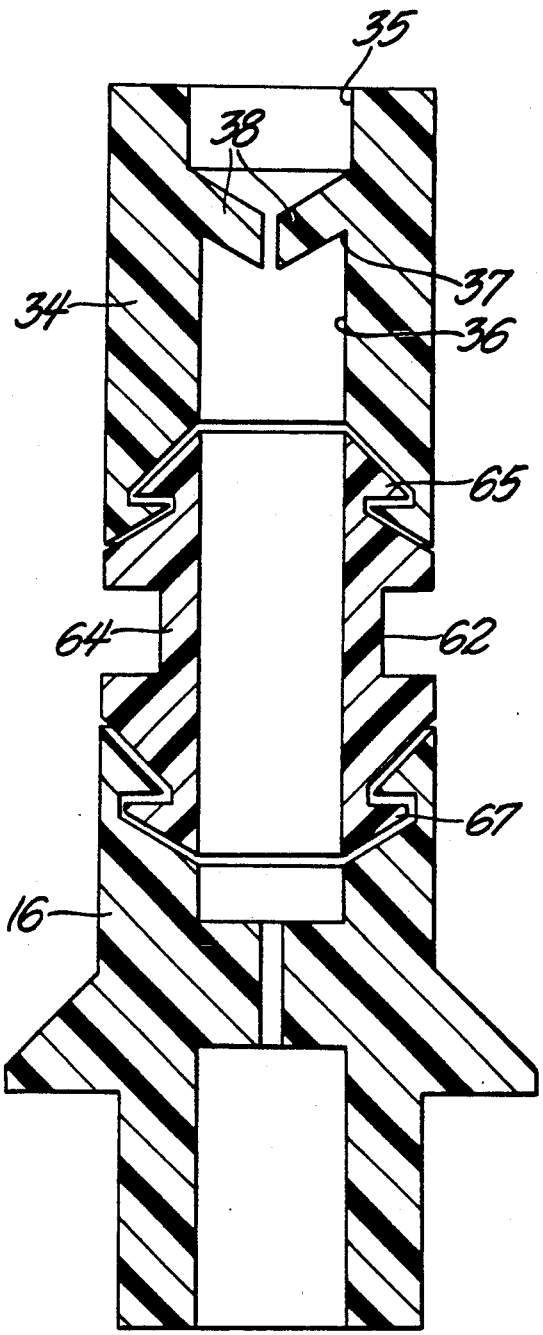
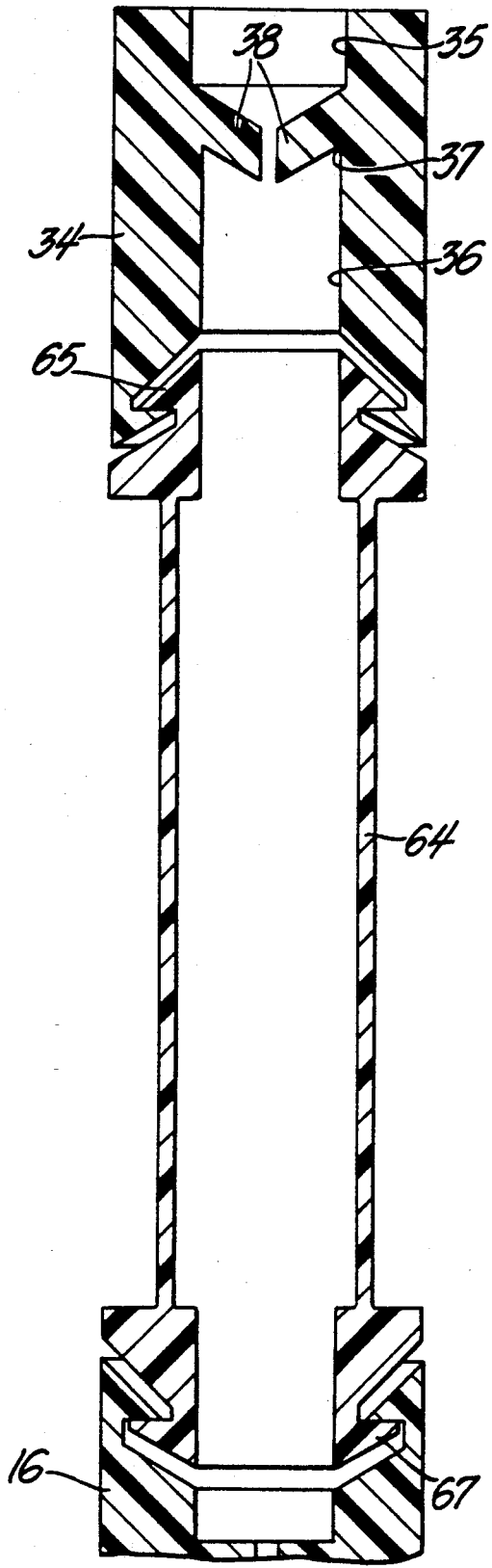
Fig. 5
Fig. 6

METHOD OF MAKING A NEEDLE SLEEVE ASSEMBLY

TECHNICAL FIELD

The invention relates to a method of making disposable needle assemblies for use in combination with a hypodermic syringe apparatus, and more specifically to a disposable needle assembly for use in combination with a catheter disposed over a needle to cap the distal end of the needle upon displacement of the needle from the catheter.

BACKGROUND OF THE INVENTION

There is a risk of exposure to infectious agents by health care workers who are continually utilizing hypodermic syringe assemblies for injecting patients with medicaments. Because of this risk, needles used by health care workers are regarded as potentially infective and are handled with extraordinary care to prevent accidental injuries. Health care workers are advised to place disposable needles in the puncture resistant containers. It has become more convenient and safe to provide capping assemblies secured to each needle for immediate capping after use of the needle.

U.S. Pat. No. 3,134,380 to Armao, issued May 26, 1964 is representative and relates to a hypodermic needle assembly which attempts to shield a used hypodermic needle after use. The Armao patent discloses a retractable needle guard which extends over the length of the needle assembly prior to use and is retracted as the needle is inserted into the patient This typical assembly includes a shield which covers a significant portion of the needle shaft during use of the needle for an injection. Hence, the typical assemblies either have less usable needle length if a conventional needle is adapted to the assembly, or the assemblies require a significantly longer needle shaft. Additionally, all these assemblies leave the tip of the needle exposed or capable of being exposed. The tip of the needle is not locked in a completely enclosed guard.

U.S. Pat. Nos. 4,978,344 and 4,994,041, both to Dombrowski et al, disclose needle and catheter assemblies. The patents disclose a needle assembly which includes a hub for connecting the assembly to a fluid conduit, i.e., the needle. The hub includes a passageway extending therethrough to receive a hollow needle in fluid communication therewith. The cap has a neutral position along the needle adjacent to the hub for exposing a length of the needle and an extended position for capping the distal tip of the needle. The needle is disposed within a passageway of the catheter assembly whereby removal of the needle from the passageway of the catheter assembly moves the cap to the extended position capping the distal tip as the cap is unseated from the catheter assembly.

SUMMARY OF THE INVENTION

The invention includes a method of forming self-capping intravenous needle assemblies adapted to receive a catheter assembly releasibly connected thereto. The method includes the steps of aligning the passageways of a hub portion and a cap of the needle assembly longitudinally with one another, securing a sheet of material to and extending between the hub portion and cap, sealing the edges of the sheet material extending between the hub portion and the cap producing an enclosed sleeve, stretching the sheet of material to a predetermined length, extending a needle through the passageways of the hub portion and cap, moving the cap and the hub adjacent one another to fold the sleeve therebetween for storing until use of the needle assembly.

The invention provides a method of forming the sleeve to connect the cap to the hub assembly and to allow subsequent automatic self-capping of intravenous needles once the catheter assembly is removed from the needle assembly.

FIGURES IN THE DRAWINGS

Advantages of the present invention will be readily appreciated as the same becomes better understood by reference to the following detailed description when considered in connection with the accompanying drawings wherein:

FIG. 1 is a longitudinal cross sectional view of a needle assembly constructed in accordance with the present invention;

FIG. 2 is a side elevational view of a catheter being completely removed from the needle of the assembly, and the capping of the distal tip of the needle;

FIG. 3 is a longitudinal elevational view of a first step of the subject invention;

FIG. 4 is a longitudinal elevational view of the second step of the subject invention;

FIG. 5 is a cross sectional view of a second embodiment of the subject invention in the second step; and FIG. 6 is a cross sectional view showing a third step of the subject invention with the second embodiment.

DESCRIPTION OF THE PREFERRED EMBODIMENT

A disposable intravenous needle assembly is generally indicated at 10 in FIGS. 1 and 2. The assembly 10 includes a combination of hypodermic needle assembly 12 and a catheter assembly 14. The hypodermic needle assembly 12 includes a hub portion 16 having an inner cup shaped surface 18 adapted to be connected to a syringe barrel 22 as shown in FIG. 1 and as in U.S. Pat. No. 4,978,344 discussed in the Background of the Invention and incorporated by reference herein. The hub portion 16 includes a passageway 24 extending therethrough. The hub portion 16 includes a radially outwardly extending flange 26 to secure the hub portion 16 to the syringe 22 with a leur-lock mechanism. Other locking mechanisms can be used to connect the hub portion 16 to the syringe 22.

A hollow metallic needle 28 includes a base 30 which is reversibly fit into the passageway 24 of the hub portion 16. The hollow needle 28 is in fluid communication with the passageway 24. The hollow needle 28 includes a distal tip 32. The distal tip 32 is a sharp pointed beveled portion of the needle 28 adapted for puncturing the skin as commonly known in the art.

The assembly 10 includes a cap 34 having a neutral position, along the needle 32 approximate to or adjacent the hub 16 for exposing the length of the needle 28 as shown in FIG. 1. The cap 34 has an extended position for capping the distal tip 32 as shown in FIG. 2. The cap 34 includes a cap passageway 35 to allow passage of the needle 28 therethrough. The cap 34 includes an inner surface 36 having one or more flanges 38 extending therefrom and angling towards the hub portion 16. The flange 38 forms closed corners 37 defined by the inner surface 36. In the extended position, the flange 38 covers the needle tip 32 and prevents the needle tip 32 from reentering the opening 35. The cap 34 includes an outer seating surface 42 for receiving the catheter assembly 14 as subsequently discussed.

The assembly 10 includes connecting means 50 for connecting the cap 34 to the hub portion 16 of the needle assembly 12 and limiting the extent the cap 34 can be extended from the hub 16. The cap 34 can extend from the hub portion 16 to the length of the needle 28 and, in combination with the flange 38 deflects the needle tip 32 into the closed corners 37. The needle tip 32 is thereafter locked under the cap 34 when it is moved to the extended position. The flange 38 in combination with the connecting means 50 provides locking means for locking the cap 34 over the distal tip 32 of the needle 28 when the tether 50 is completely extended.

More specifically, the connecting means 50 is in the form of an expandable sleeve 64 interconnecting the hub portion 16 and the cap 34 for perfecting a seal and closure about the entire length of the needle 28 when the cap 24 is in the extended position as shown in FIG. 2. The sleeve 64 is formed of an organic polymeric sheet material or formed of synthetic material having a stretched predetermined length of extension. Also, the sleeve 64 may be formed of a woven sheet impermeable to water. The sleeve 64 is formed by forming two sheets 62 of material about the hub portion 16 and cap 24, sealing the edges thereof, and securing same to the hub portion and cap 24, as subsequently discussed.

The catheter assembly 14 includes a shaft portion 40 disposed about the exposed length of the needle 28 and exposing the distal tip 32. In this position, the distal tip 32 can initiate a puncture through a patient's skin and into a vessel so that the shaft portion 40 of the catheter 14 can enter the patient's blood vessel.

The catheter assembly 14 includes a catheter hub 44 connected to the shaft portion 40 and having an inner surface for releasibly seating on the cap seating surface 42 whereby removal of the needle 28 from the shaft 40 moves the cap 34 to the extended position having the distal tip 32 of the needle 28 as the hub 44 of the catheter assembly 14 is unseated from the seating surface 42 of the cap 34, as disclosed in the referenced patent. The distal tip 32 of the needle 28 is simultaneously capped as the needle 28 is removed from the catheter assembly 14. A person administering the injection need not first remove the needle assembly 12 from the catheter assembly 14, and then independently cap the distal tip or end 32 of the needle 28, but rather the needle 28 is capped in a single motion of removing the needle 28 from the catheter assembly 14 once the patient is catheterized. The sleeve 64 maintains the cap 34 locked against the distal tip 32.

The seating surface 42 provides an outer cylindrical or frustoconical surface of the cap 34. The hub 44 of the catheter assembly 14 includes an inner complimenting surface 46 defining a seat in friction fit, or other reversible method of seating or connecting the seating surfaces, over the seating surface 42 of the cap 34 when the cap 34 is in the neutral position shown in FIG. 1. The hub 44 of the catheter assembly 14 includes a radially outwardly extending annular flange 48. The flange 48 allows for a leur lock of the catheter, such as to another syringe.

In operation, the catheter assembly 14 is seated over cap 34, both being disposed adjacent the hub portion 16. After catheterization of the patient, the hub portion 16 is moved away from the catheter 14 withdrawing the needle portion 28 from the catheter 14 and extending the sleeve 64. The hub portion 16 may or may not include a syringe assembly 22. Once the cap 34 is extended so that the flange 38 is covered by the distal tip 32 in the closed corner 37, the length of the sleeve 64 limits the further extending of the cap 34 such that the flange 38 deflects the needle tip 32 from reentering the cap passageway 35 and into the closed corners 37 thereby irreversibly capping the needle 28. Upon further removal of the assembly 10 away from the catheter 14, the cap 34 becomes unseated from the second hub portion 44 of the catheter 14 as shown in FIG. 2. When in a single motion, the withdrawal of the remainder of the assembly 10 from the catheter 14 extends in and the cap member 34 over the distal tip 32 while simultaneously releasing the catheter 14 therefrom. U.S. Pat. No. 4,978,344 set forth in the Background of the Invention is incorporated by reference herein which shows the general construction of the needle and catheter assemblies.

The invention includes a method of forming the assembly 10, and more specifically the sleeve 64. The method includes the steps of placing the hub portion 16 and cap 34 along a long pin 60 such that the pin 60 extends through the passageway 24, 35 (FIG. 3). Alternatively, the hub portion 16 and cap 34 may be aligned about the needle 28. Thereafter, a sheet of material 62 is secured to the hub portion 16 and cap 34. The sheets of material 62 may to connected to the hub portion 16 and cap 34 either by welding or adhesion 63 (FIGS. 3-4) or locking by use of a flange 65, 67 as shown in FIGS. 5-6. The edges 66 of the sheet of material 62 are sealed to one another to produce an enclosed sleeve 64. In the preferred embodiment, two sheets of the material 62 are extended between and connected to the hub portion 16 and cap 34 with the hub portion 16 and cap 34 between the two sheets 62. Thereafter, the edges 66 of the two sheets are welded to one another to form an enclosed sleeve 64 about the hub portion 16 and cap 34. The excess material 62 is cut away and removed from the welded seam 68. In the preferred embodiment, the sheets of material are comprised of an organic polymeric material.

The formed sleeve 64 may be cold or hot stretched to a predetermined length greater than the sleeve formation length as shown in FIG. 6. During the stretching, the diameter of the sleeve 64 is reduced which also reduces the size of the seam 68. After stretching to the predetermined length, the finished and assembled hub portion 16, sleeve 64 and cap 34 are transferred from the pin 60 to a metal intravenous needle 28. The hub portion 16 is fixedly attached to the needle assembly 12 by friction, flange snap-fit, welding or adhesive as commonly known in the art. Once attached to the needle 28, the cap 34 is moved towards the hub portion 16. Because of the smaller diameter, the sleeve 64 folds and stores into the cap 34. Alternatively, the sleeve 64 may fold into the hub portion 16. Thereafter, the catheter assembly 14 may be slid over the needle 28 and the catheter hub 44 secured to the needle hub portion 16.

The sleeve 64 is made of the sheets of organic polymeric material. Such material 62 can be either capable of cold stretching to a predetermined or maximum length which length is maintained once stretched. Alternatively, such material 62 may be capable of heat stretching to the predetermined length. The welding occurs by application of heat to weld the two sheets of material to one another.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A method of forming self-capping intravenous needle assemblies (10) adapted to receive a catheter assembly (14) releasably connected to the needle assembly (10), the method including the steps of:
   aligning the passageways (24, 35) of a hub portion (16) and a cap (34) of the needle assembly (12) longitudinally with one another,
   securing a sheet of material (62) to and extending between the hub portion (16) and cap (34),
   sealing the edges of the sheet of material extending between the hub portion (16) and cap (34) producing an enclosed sleeve (64),
   extending a needle (28) through the passageways of the hub portion (16) and cap (34), and moving the cap (34) and hub portion (16) adjacent one another to fold the sleeve (64) therebetween for storing until use of the needle assembly.

2. A method as set forth in claim 1 further including stretching the sleeve of material (62) to a predetermined length, prior to folding the sleeve.

3. A method as set forth in claim 2 further including aligning two sheets of material (62) extending between and connected about the hub portion (16) and cap (34).

4. A method as set forth in claim 3 further including welding the two sheets (62) of material to one another along the edges thereof.

5. A method as set forth in claim 4 further including aligning two sheets of organic polymeric material (62).

6. A method as set forth in claim 5 further including transferring the hub portion (16), cap (34) and sleeve (64) after stretching to an intravenous needle (28).

7. A method as set forth in claim 6 further including attaching the hub portion (16) to the needle (28).

8. A method as set forth in claim 7 further including sliding the cap (34) toward the hub portion (16) along the needle (28) to compact the sleeve (64) between the hub portion (16) and the cap (34).

9. A method as set forth in claim 8 further including cold stretching the sleeve (64) of organic polymeric material to the predetermined length.

10. A method as set forth in claim 8 further including stretching the sleeve (64) of organic polymeric material to the predetermined length upon application of heat.

11. A method as set forth in claim 8 further including sliding a catheter assembly (14) over the needle (28) and placing a catheter hub (44) of a catheter assembly (14) adjacent the cap (34) and secured thereto to cause the cap (34) to slide along the needle (28) secured with the catheter hub (44) after injection of the needle and catheter.

* * * * *